(12) United States Patent
Fukushima (10) Patent No.: US 8,569,324 B2
(45) Date of Patent: Oct. 29, 2013

(54) POTENTIATOR FOR RADIATION THERAPY COMPRISING PYRIDINE DERIVATIVE AS ACTIVE INGREDIENT

(75) Inventor: Masakazu Fukushima, Tokushima (JP)

(73) Assignee: Taiho Pharmaceutical Co., Ltd., Tokyo (JP)

( * ) Notice: Subject to any disclaimer, the term of this patent is extended or adjusted under 35 U.S.C. 154(b) by 128 days.

(21) Appl. No.: 12/978,743

(22) Filed: Dec. 27, 2010

(65) Prior Publication Data

US 2011/0091016 A1 Apr. 21, 2011

Related U.S. Application Data

(62) Division of application No. 11/910,150, filed as application No. PCT/JP2006/306961 on Mar. 31, 2006, now abandoned.

(30) Foreign Application Priority Data

Apr. 1, 2005 (JP) .................................. 2005-105938
Jul. 28, 2005 (JP) .................................. 2005-219119

(51) Int. Cl.
*A61K 31/435* (2006.01)

(52) U.S. Cl.
USPC ........................................................ 514/277

(58) Field of Classification Search
USPC ................. 514/277, 241, 274; 424/4
See application file for complete search history.

(56) References Cited

U.S. PATENT DOCUMENTS

| 5,155,113 | A | 10/1992 | Fujii |
| 2004/0265813 | A1 | 12/2004 | Takechi et al. |
| 2006/0116345 | A1 | 6/2006 | Uchida et al. |
| 2008/0275071 | A1 | 11/2008 | Fukushima |
| 2009/0137640 | A1 | 5/2009 | Fukushima |
| 2009/0281105 | A1 | 11/2009 | Fukushima |

FOREIGN PATENT DOCUMENTS

| JP | 61-022016 | 1/1986 |
| JP | 61-109719 | 5/1986 |
| JP | 63-250324 | 10/1988 |

OTHER PUBLICATIONS

Yasumasa Nishimura, "Rationale for Chemoradiotherapy", Int. J. Clin. Oncol., vol. 9, No. 6, 2004, pp. 414-490.
Gilles Calais, et al., "Randomized Trial of Radiation Therapy Versus Concomitant Chemotherapy and Radiation Therapy for Advance-Stage Oropharynx Carcinoma", Journal of the National Cancer Institute, vol. 91. No. 24, Dec. 15, 1999, pp. 2081-2086.
Branislav Jeremic, et al., "Hyperfractionated Radiation Therapy With or Without Concurrent Low-Dose Daily Cisplatin in Locally Advanced Squamous Cell Carcinoma of the Head and Neck: A Prospective Randomized Trial", Journal of Clinical Oncology, vol. 18, No. 7, Apr. 2000, pp. 1458-1464.
M. Al-Sarraf, et al., "Progress Report of Combined Chemoradiotherapy Versus Radiotherapy Alone in Patients With Esophageal Cancer: An Intergroup Study", Journal of Clinical Onclogy, vol. 15, No. 1, Jan. 1997, pp. 277-284.
C. G. Moertel, et al., "Therapy of Locally Unresectable Pancreatic Carcinoma: A Randomized Comparison of High Dose (6000 Rads) Radiation Alone, Moderate Dose Radiation (4000 Rads + 5-Fluorouracil), and High Dose Radiation + 5-Fluorouracil", Cancer, vol. 48, 1981, pp. 1705-1710.
William Sause, et al., "Final Results of Phase III Trial in Regionally Advanced Unresectable Non-Small Cell Lung Cancer", Clinical Investigations, vol. 117, No. 2, 2000, pp. 358-364.
K. M. Tveit, et al., "Randomized Controlled Trial of Postoperative Radiotherapy and Short-Term Time-Scheduled 5-Fluorouracil Against Surgery Alone in the Treatment of Dukes B and C Rectal Cancer", British Journal of Surgery, vol. 84, 1997, pp. 1130-1135.
Koji Harada, et al., "Combined effects of the oral fluoropyrimidine anticancer agent, S-1 and radiation on human oral cancer cells", Oral Oncology, vol. 40, No. 7, XP004511987, Aug. 1, 2004, pp. 713-719.
Hiroaki Iwase, et al., "Esophageal cancer with colonic metastasis successfully treated by chemoradiotherapy followed by chemotherapy with S-1 and cisplatin", International Journal of Clinical Oncology, vol. 9, XP003000958, Jan. 1, 2004, pp. 398-402.
Tsunehiro Takahashi, et al., "Histological Complete Response in a Case of Advanced Gastric Cancer Treated by Chemotherapy with S-1 Plus Low-dose Cisplatin and Radiation", Japanese Journal of Clinical Oncology, vol. 33, No. 11, XP003000956, Jan. 1, 2003, pp. 584-588.

(Continued)

Primary Examiner — Kevin E Weddington
(74) Attorney, Agent, or Firm — Oblon, Spivak, McClelland, Maier & Neustadt, L.L.P.

(57) ABSTRACT

The present invention relates to a radiotherapy enhancer that can reduce the radiation dose and adverse drug reactions when used in combination with a cancer radiotherapy. There is provided a radiotherapy enhancer comprising, as an active ingredient, a pyridine derivative represented by general formula (1):

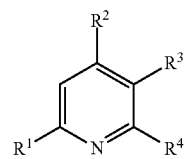

(1)

wherein $R^1$, $R^2$, and $R^4$ may be the same or different from one another and represent a hydrogen atom, hydroxy group, or protected hydroxy group, excluding the case where $R^1$, $R^2$, and $R^4$ are all a hydrogen atom, and $R^3$ represents a halogen atom, amino group, carboxyl group, carbamoyl group, cyano group, nitro group, alkyl group having 1 to 6 carbon atoms, alkenyl group having 2 to 6 carbon atoms, or carbonyl group containing an alkoxy group having 1 to 6 carbon atoms).

13 Claims, 2 Drawing Sheets

(56) References Cited

OTHER PUBLICATIONS

Yukito Ichinose, et al., "S-1 Plus Cisplatin Combination Chemotherapy in Patients with Advanced Non-Small Cell Lung Cancer: A multi-Institutional Phase II Trial", vol. 10, XP003000957, Dec. 1, 2004, pp. 7860-7864.

Kazunori Yoneda, et al., "The inhibitory action of BOF-A2, a 5-fluorouracil derivative, on squamous cell carcinoma", Cancer Letters, vol. 137, No. 1, XP002536212, Mar. 22, 1999, pp. 17-25.

J. M. Brown, et al., "Structure-activity relationships for tumour radiosensitization by analogues of nicotinamide and benzamide", International Journal of Radiation Biology, vol. 59, No. 3, XP009119752 1991, pp. 739-748.

Kawahara et al, British Journal of Cancer, 2001, 85(7), 939-943.

Altman et al, The Cancer Dictionary, 1992, pp. 231-232.

Y. Sakata, Eur. J. Cancer 1998, 34, 1715-1720.

U.S. Appl. No. 13/319,951, filed Nov. 10, 2011, Fukushima.

European Office Action issued Apr. 6, 2011, in Patent Application No. 06 730 909.6.

Y Shibamoto, et al., "Combined effect of clinically relevant doses of emitefur, a new 5-fluorouracil derivative, and radiation in murine tumours", British Journal of Cancer, vol. 74, No. 11, 1996, pp. 1709-1713.

U.S. Appl. No. 13,716,452, filed Dec. 17, 2012, Fukushima.

POTENTIATOR FOR RADIATION THERAPY COMPRISING PYRIDINE DERIVATIVE AS ACTIVE INGREDIENT

TECHNICAL FIELD

The present invention relates to a radiotherapy enhancer that can reduce the radiation dose and adverse drug reactions, when used in combination with cancer radiotherapy.

BACKGROUND ART

Conventionally, surgical therapy, chemotherapy, immunotherapy, thermotherapy, and radiotherapy have been performed for the treatment of cancer (malignant tumor). Radiotherapy is often performed for various types of cancers such as gastric cancer, colorectal cancer, pancreatic cancer, head and neck cancer, esophageal cancer, lung cancer, and breast cancer that are advanced to stage III or IV. However, long-term treatment using radiation alone (a total radiation dose of 40 to 60 Gy is currently used in clinical setting) is thought to be difficult due to adverse drug reactions in the digestive system, such as hematological toxicity and dry mouth, and its clinical effect (antitumor effect) is therefore insufficient. To achieve a high antitumor effect, chemoradiotherapy using chemotherapeutic drugs and radiation in combination has recently been introduced as one of standard therapies, and it is said that its treatment results are better than those of therapies using radiation alone or chemotherapy alone (Non-Patent Document 1). For example, it has been disclosed that a combination of carboplatin/fluorouracil and radiation (Non-Patent Document 2) or cisplatin and radiation (Non-Patent Document 3) for the treatment of head and neck cancer, a combination of fluorouracil/cisplatin and radiation (Non-Patent Document 4) for the treatment of esophageal cancer, a combination of fluorouracil and radiation (Non-Patent Document 5) for the treatment of pancreatic cancer, and a combination of cisplatin/vinblastine and radiation (Non-Patent Document 6) for the treatment of non-small cell lung cancer significantly prolong the survival time as compared with therapies using radiation alone. Furthermore, a report has shown that the recurrence rate was lower, and the survival time is longer in patients with rectal cancer who postoperatively underwent chemoradiotherapy than in patients who did not (Non-Patent Document 7). However, since adverse drug reactions of chemotherapeutic drugs themselves occur in the conventional use of chemotherapeutic drugs and radiotherapy in combination, the medial practice may have to be discontinued as a result. Satisfactory effect of reducing adverse drug reactions has not been obtained either.

Various attempts have been made to develop a radiation sensitizer that reduces the radiation dose and adverse drug reactions without compromising the therapeutic effect of radiotherapy. For example, certain types of nitroimidazole derivatives are known as radiation sensitizers, and compounds such as misonidazole and etanidazole have been developed. However, these compounds have not been used in practice due to their too severe neurotoxicity at doses at which sensitization activity can be obtained and the like. While combination use of a drug that enhances radiation sensitivity is desired in the treatment of radiation-resistant tumors, this neurotoxicity has become problematic in the development of many of the previously reported radiotherapy enhancers (radiation sensitizers, etc.).

[Non-Patent Document 1] International Journal of Clinical Oncology, Vol. 9, No. 6, (2004): 414-490

[Non-Patent Document 2] Calais et al., J. Natl. Cancer Inst. 91 (1999): 2081-2086

[Non-Patent Document 3] Jeremic B, et al., J. Clin. Oncol. 18 (2000): 1458-1464

[Non-Patent Document 4] Al-Sarraf M, et al., J. Clin. Oncol. 15 (1997): 277-284

[Non-Patent Document 5] Moertel C G, et al., Cancer 48 (1981): 1705-1710

[Non-Patent Document 6] Sause W, et al., Chest 117 (2000): 358-364

[Non-Patent Document 7] Tveit K M, et al., Br. J. Cancer 84 (1997): 1130-1135

DISCLOSURE OF THE INVENTION

Accordingly, an object of the present invention is to provide a radiotherapy enhancer that can reduce the radiation dose and adverse drug reactions when used in combination with cancer radiotherapy.

Accordingly, the inventors of the present invention investigated radiotherapy enhancing effects of various substances. As a result, they found that a pyridine derivative represented by the following general formula (1) that is known as an antitumor activity enhancer of an antitumor agent had an excellent radiotherapy enhancing effect and can reduce the radiation dose and adverse drug reactions when used in combination with radiotherapy, and accomplished the present invention.

Specifically, the present invention provides a radiotherapy enhancer comprising, as an active ingredient, a pyridine derivative represented by general formula (1):

wherein $R^1$, $R^2$, and $R^4$ may be the same or different from one another and represent a hydrogen atom, hydroxy group, or protected hydroxy group, excluding the case where $R^1$, $R^2$, and $R^4$ are all a hydrogen atom, and $R^3$ represents a halogen atom, amino group, carboxyl group, carbamoyl group, cyano group, nitro group, alkyl group having 1 to 6 carbon atoms, alkenyl group having 2 to 6 carbon atoms, or carbonyl group containing an alkoxy group having 1 to 6 carbon atoms.

Furthermore, the present invention provides cancer radiotherapy characterized in that the above-described radiotherapy enhancer and radiation are used in combination.

Furthermore, the present invention provides use of the pyridine derivative represented by the above-described general formula (1) for the production of a radiotherapy enhancer.

EFFECT OF THE INVENTION

Since use of the radiotherapy enhancer of the present invention and radiotherapy in combination achieves excellent cancer therapeutic effect at a lower radiation dose and reduces adverse drug reactions, long-term effective cancer treatment is enabled.

BEST MODE FOR CARRYING OUT THE INVENTION

The term "protected hydroxy group" in $R^1$, $R^2$, and $R^4$ in the pyridine derivative (1) used for the radiotherapy enhancer of the present invention means a protected hydroxy group that is easily hydrolyzed within blood and tissues of mammals including humans to release a corresponding hydroxy group compound, and the protected hydroxy group is not limited so long as it is a commonly known group in which a hydroxy group is protected by the formation of an ester. Examples thereof include acyloxy groups, such as alkanoyloxy groups, arylcarbonyloxy groups, heteroarylcarbonyloxy groups, and so forth that have 1 to 20 carbon atoms. More specific examples thereof include acetoxy group, propionyloxy group, butyryloxy group, isobutyryloxy group, varelyloxy group, pivaloyloxy group, lauroyloxy group, myristoyloxy group, palmitoyloxy group, stearoyloxy group, benzoyloxy group, naphthoyloxy group, toluoyloxy group, 2-furoyloxy group, 3-furoyloxy group, 2-thenoyloxy group, 3-thenoyloxy group, nicotinoyloxy group, isonicotinoyloxy group, and so forth. Examples of the halogen atom represented by $R^3$ include chlorine atom, fluorine atom, bromine atom, and iodine atom. Examples of the alkyl group having 1 to 6 carbon atoms include straight or branched alkyl groups having 1 to 6 carbon atoms such as methyl group, ethyl group, propyl group, isopropyl group, butyl group, t-butyl group, pentyl group, and hexyl group. Examples of the alkenyl group having 2 to 6 carbon atoms include alkenyl groups having 2 to 6 carbon atoms such as vinyl group, allyl group, 2-butenyl group, 3-butenyl group, 1-methylallyl group, 2-pentenyl group, and 2-hexenyl group. Examples of the carbonyl group containing an alkoxy group having 1 to 6 carbon atoms include straight or branched carbonyl groups containing an alkoxy group having 1 to 6 carbon atoms such as methoxycarbonyl group, ethoxycarbonyl group, propoxycarbonyl group, isopropoxycarbonyl group, t-butoxycarbonyl group, butoxycarbonyl group, pentyloxycarbonyl group, and hexyloxycarbonyl group.

It is preferable that any two of $R^1$, $R^2$, and $R^4$ in the general formula (1) represent hydroxy group or protected hydroxy group, and the remaining one represents a hydrogen atom. Specifically, it is preferable that $R^1$ and $R^2$ may be the same or different from each other and represent hydroxy group or protected hydroxy group, and $R^4$ represents a hydrogen atom, or that $R^1$ and $R^4$ may be the same or different from each other and represent hydroxy group or protected hydroxy group, $R^2$ represents a hydrogen atom. Of these, it is preferable that $R^1$ and $R^2$ represent hydroxy group, and $R^4$ represents a hydrogen atom, or that $R^1$ and $R^4$ represent hydroxy group, and $R^2$ represents a hydrogen atom.

As $R^3$, a halogen atom or cyano group is more preferred, with a chlorine atom or cyano group being more preferred.

Of compounds represented by the formula (1), a compound in which $R^1$ and $R^2$ are hydroxy group, $R^3$ is a chlorine atom, and $R^4$ is a hydrogen atom, i.e., 5-chloro-2,4-dihydroxypyridine (CDHP) is preferred. Furthermore, a compound in which $R^1$ and $R^4$ are hydroxy group, $R^3$ is cyano group, and $R^2$ is a hydrogen atom, i.e., 3-cyano-2,6-dihydroxypyridine (CNDP) is preferred.

The compound represented by the formula (1) can be produced by the method described in Japanese Unexamined Patent Publication No. 62-155215, for example. The compound represented by the formula (1) is known to have an action of elevating concentrations of 5-FU based antitumor agents such as tegafur and 5-FU in an organism by selectively inhibiting dihydropyrimidine dehydrogenase (DPD), a 5-FU catabolizing enzyme abundantly distributed in the liver, and thereby enhancing the antitumor effect of 5-FU based antitumor agents. However, the action of the compound represented by the formula (1) on radiotherapy is unknown.

Combined use of the compound represented by the formula (1) and radiotherapy markedly enhances the cancer therapeutic effect of radiation compared with use of radiotherapy alone. Therefore, the compound of formula (1) is useful as a radiotherapy enhancer. Furthermore, since an adequate therapeutic effect on cancer can be obtained at a lower radiation dose as a result of the enhanced effect of radiotherapy, the compound of formula (1) can also act as an agent for reducing the radiation dose in cancer treatment. Furthermore, since prolonged high-dose radiotherapy causes adverse drug reactions such as hematological toxicity, digestive toxicity, anorexia, malaise, and body weight loss, some patients could not receive long-term treatment previously. However, since combination of the compound of formula (1) and radiotherapy can reduce the radiation dose and hence reduces these adverse drug reactions, longer-term radiotherapy is enabled, resulting in improved therapeutic effects on cancer. Furthermore, radiotherapy causes severe dermatitis in the skin at the radiation-irradiated site, with skin disorders such as redness, dryness, skin abrasion, blister, and erosion, and may cause pigmentation, joint contracture, swelling of extremities, and the like later. However, combined use of the compound of formula (1) can prevent or relieve skin adverse drug reactions of radiation. Therefore, the compound of formula (1) is also useful as an agent for preventing or relieving adverse drug reactions of radiation, particularly as an agent for preventing or relieving skin adverse drug reactions of radiation.

The term "radiotherapy enhancer" used in the present specification refers to a drug that enhances (improves) radiation sensitivity (also referred to as radiation sensitivity enhancer, radiation sensitizer, or radiation sensitizing agent) irrespective of the mechanism of action.

Furthermore, cancer radiotherapy intended in the present invention is commonly used in this technical field and can be performed according to protocols known to those skilled in the art. For example, irradiation with cesium, iridium, iodine, or cobalt is included in the above-mentioned cancer radiotherapy. Cancer radiotherapy may be systemic irradiation (for the treatment of acute leukemia, malignant lymphoma, and some solid cancers), but local irradiation of tumor sites or tissues (irradiation of the abdomen, lungs, liver, lymph nodes, head or the like for solid cancers) is preferred. Cancer radiotherapy is commonly divided into 25 to 30 fractions (over about 5 to 6 weeks) and performed for 2 to 3 minutes per day.

The radiotherapy enhancer of the present invention can be used as an auxiliary agent in a cancer radiotherapy of malignant tumors that are not originally sensitive to radiation or have acquired radiation resistance as a result of radiotherapy. Furthermore, the radiotherapy enhancer of the present invention can reduce the radiation dose used in the therapy by enhancing the radiation sensitivity of tumor cells (can reduce the dose to ½ to ⅓ of the conventional dose, for example). Therefore, adverse drug reactions due to radiation injury inevitably associated with radiotherapy (for example, stomatitis, myelopathy, radiation ulcer, radiation pneumonia, skin disorders, etc.) can be reduced. Furthermore, since the treatment period (exposure time) can be made longer than a period specified in usual protocols (can be prolonged 1.5- to 2-fold, for example), an excellent antitumor effect can be obtained.

The radiotherapy enhancer of the present invention is administered at the time of radiotherapy, either before or after radiotherapy. Furthermore, since the radiotherapy enhancer of the present invention enhances the effect of cancer radiotherapy as described above, it may be used in combination with other antitumor agents. Examples of such antitumor agents include platinum drugs, taxane drugs, vinca alkaloid drugs, topoisomerase inhibitors, antimetabolites, alkylating agents, and so forth. More specific examples include one type or two or more types of antitumor agents such as cisplatin, carboplatin, oxaliplatin, Taxol, Taxotere, vincristine, vinblastine, vinorelbine, vindesine, irinotecan hydrochloride, topotecan, etoposide, teniposide, doxorubicin, tegafur, gemcitabine, cytarabine, methotrexate, Alimta, cyclophosphamide, adriamycin, and mitomycin. These antitumor agents are used in combination, taking into account the patient's age and sex, severity of symptoms/adverse drug reactions, drug incompatibility, and the like.

The radiotherapy enhancer of the present invention can be produced in the form of a usual pharmaceutical preparation using pharmaceutically acceptable carriers such as, for example, fillers, extenders, binders, moisturizing agents, disintegrating agents, surfactants, lubricants, and excipients. Examples of this pharmaceutical preparation include tablet, pill, powder, solution, suspension, emulsion, granule, capsule, suppository, injection (solution, suspension, etc.), ointment, and so forth. The radiotherapy enhancer of the present invention can be prepared in the form of tablet using, for example, excipients such as lactose, sucrose, sodium chloride, glucose, urea, starch, calcium carbonate, kaolin, crystalline cellulose, and silicic acid, binders such as water, ethanol, propanol, simple syrup, glucose solution, starch solution, gelatin solution, carboxymethylcellulose, shellac, methylcellulose, potassium phosphate, and polyvinylpyrrolidone, disintegrating agents such as dry starch, sodium alginate, powdered agar, powdered laminaran, sodium hydrogencarbonate, calcium carbonate, polyoxyethylene sorbitan fatty acid esters, lauryl sodium sulfate, monoglyceride stearate, starch, and lactose, disintegration inhibitors such as sucrose, stearin, cocoa butter, and hydrogenated oils, absorption promoters such as quaternary ammonium base and lauryl sodium sulfate, moisturizing agents such as glycerine and starch, adsorbents such as starch, lactose, kaolin, bentonite, and colloidal silicic acid, lubricants such as purified talc, stearates, powdered boric acid, and polyethylene glycol, and the like. Furthermore, tablet can be coated with a usual coating as required to prepare, for example, a sugar-coated tablet, gelatin-encapsulated tablet, enteric-coated tablet, film coated tablet, double-layer tablet, or multilayer tablet. The radiotherapy enhancer of the present invention can be prepared in the form of pill using, for example, excipients such as glucose, lactose, starch, cacao butter, hydrogenated vegetable oil, kaolin, and talc, binders such as gum arabic powder, tragacanth powder, gelatin, and ethanol, disintegrating agents such as powdered laminaran and powdered agar, and the like. The radiotherapy enhancer of the present invention can be prepared in the form of suppository using, for example, polyethylene glycol, cacao butter, higher alcohols, higher alcohol esters, gelatin, semi-synthesized glyceride, and the like. Capsule is prepared according to usual methods by usually mixing an active ingredient compound with various carriers mentioned above as examples and filling them in a hard gelatin capsule, soft capsule, or the like. When the radiotherapy enhancer of the present invention is prepared as an injection, the solution, emulsion, or suspension thereof is sterilized and is preferably isotonic with blood. When these forms are prepared, a wide variety of known diluents can be used, and examples thereof include water, ethyl alcohol, macrogol, propylene glycol, polyethoxylated isostearyl alcohol, polyoxyethylene sorbitan fatty acid esters, and so forth. In this case, sodium chloride, glucose, or glycerine in an amount sufficient to prepare an isotonic solution may be contained in the pharmaceutical preparation, or usual solubilizing agents, buffers, soothing agents, and the like may be added. Furthermore, if necessary, coloring materials, preservatives, flavors, flavoring agents, sweeteners, and the like or other drugs may be contained in the pharmaceutical preparation. The radiotherapy enhancer of the present invention can be prepared in the form of paste, cream, or gel by using white petrolatum, paraffin, glycerine, cellulose derivatives, polyethylene glycol, silicon, bentonite, or the like as a diluent.

The total amount of the above-described compound of formula (1) to be contained in the pharmaceutical preparation is not particularly limited and suitably selected in a wide range, but 1 to 70% by mass of the pharmaceutical preparation is usually desirable.

The administration method of the above-described pharmaceutical preparation is not particularly limited and determined depending on the dosage form, the patient's age, sex, and other conditions, severity of the disease, and the like. For example, oral administration as a tablet, pill, solution, suspension, emulsions, granule, or capsule is particularly preferred.

The dose of the above-described pharmaceutical preparation is suitably selected depending on the dosing regimen, patient's age, sex, and other conditions, severity of the disease, and the like. In oral administration, the dose of the compound of formula (1) as the active ingredient is usually about 0.05 to 100 mg per kg body weight, preferably about 0.1 to 50 mg. The dose of the above-described pharmaceutical preparation can be divided and administered 1 to 4 times daily.

An excellent cancer treatment method can be provided by using the radiotherapy enhancer of the present invention and radiotherapy in combination. Tumors for which this treatment method can be used are not particularly limited. This method is particularly suitable for cancers with high radiation sensitivity. However, since the enhancer of the present invention can also increase radiation sensitivity of cancers that are considered to have low sensitivity, improvement of the effect of cancer radiotherapy can be expected. Examples of such cancers include head and neck cancer, esophageal cancer, gastric cancer, colorectal cancer, liver cancer, gallbladder/bile duct cancer, pancreatic cancer, lung cancer, breast cancer, bladder cancer, prostate cancer, cervical cancer, brain tumor, malignant lymphoma, acute leukemia, chronic leukemia, medulloblastoma, retina retinoblastoma, neuroblastoma, Wilms' tumor, Hodgkin's disease, multiple myeloma, plasmacytoma, thymoma, basal cell cancer, squamous cancer, Ewing's tumor, thyroid cancer, ovary cancer, salivary gland cancer, teratoma, malignant melanoma, neuroglioma, renal cell carcinoma, osteosarcoma, and so forth. Of these, head and neck cancer, esophageal cancer, gastric cancer, colorectal cancer, liver cancer, lung cancer, pancreatic cancer, and breast cancer are preferred, cancer types that can be hardly resected such as head and neck cancer, esophageal cancer, liver cancer, lung cancer, and pancreatic cancer are more preferred, and lung cancer and pancreatic cancer are particularly preferred.

EXAMPLES

The present invention will be explained more specifically with reference to the following test examples and comparative examples. However, the scope of the present invention is not limited to these examples.

Test Example 1

(a) Preparation of test solution: 5-Chloro-2,4-dihydroxypyridine (CDHP) was suspended in a 0.5% (W/V) hydroxypropylmethylcellulose (HPMC) solution at concentrations of 0.25 and 2.5 mg/mL, and the suspension was stirred with a stirrer at room temperature for about 10 minutes and ultrasonicated for about 5 minutes with ice cooling to obtain a drug solution of 2.5 or 25 mg/kg/day as CDHP.

(b) Method for Radiation (X-ray) irradiation: Local irradiation was performed on a human tumor strain transplanted into the right femoral region of the mouse using MBR-1505R Type 2 X-ray Irradiation System of Hitachi Medical Corporation under an irradiation condition (irradiation position) so that exposure per mouse should be 2 Gy or 5 Gy. To prevent systemic irradiation, mice were placed in a storage box made of lead so that only their right leg should be exposed to radiation.

(c) Test: The human lung cancer strain (LC-11) subcutaneously transplanted into the back of a BALB/cA-nu mouse and grown beforehand were removed, cut into small fragments of about $2 \times 2$ mm$^2$ with scissors in physiological saline, and subcutaneously transplanted into the right femoral region of 5 to 6-week-old mice of the same strain with a transplantation needle. The mice were bred for at least 1 to 2 weeks and divided into the control group, the radiation alone group, the drug alone group, and the drug plus radiation group, so that the tumor volume and standard deviation (S.D.) in each group (n=6 per group) should be as uniform as possible. Then, drug administration and X-ray irradiation were initiated. The drug treatment group was orally administered with 0.1 mL each of the above-described CDHP drug solution per body weight 10 g once daily for 14 consecutive days using a sonde for oral administration. The radiation group was irradiated with 2 Gy or 5 Gy of X-ray within about 1 hour after administration of the CDHP drug solution in the above-described manner on day 1, at the start of the test, and on day 8. Tumor-bearing mice in the control group (non-radiation/non-drug treatment group) and the radiation alone group were orally administered with 0.5% HPMC solution alone in the same manner for 14 consecutive days.

Figure 1:
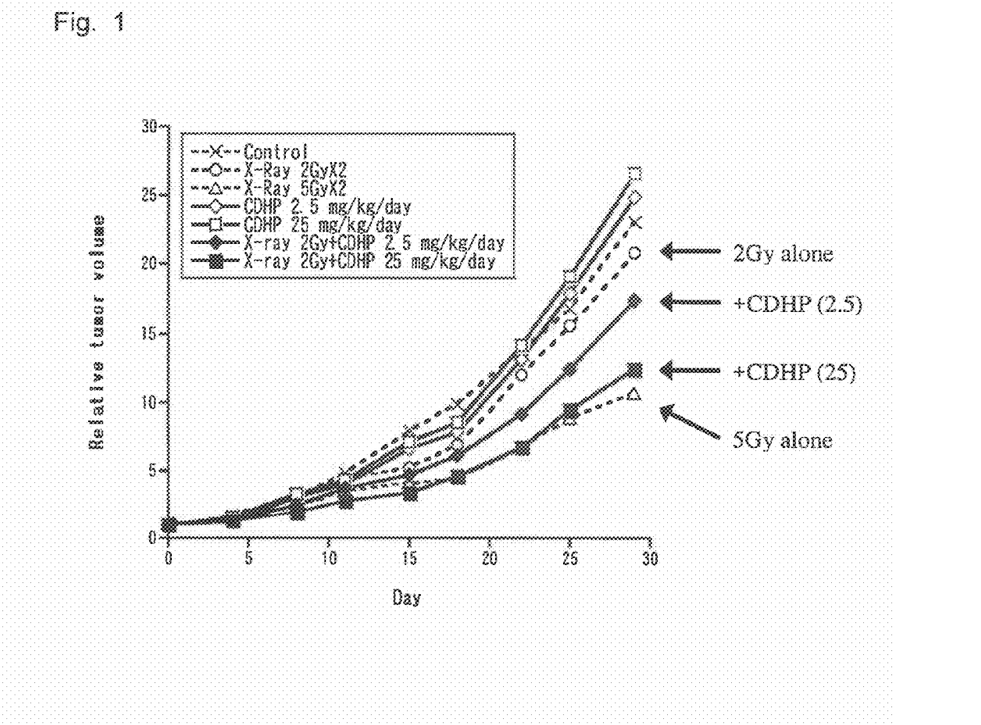
FIG. 1 shows the tumor volume ratios (relative tumor volumes) to the initial tumor volumes in Test Example 1.

By using the following numerical formula 1, the tumor volume of each mouse in each group was obtained prior to the start of treatment experiment, on days 3, 5, 8 (1 week later) and 11 during the treatment period, and days 15 (2 weeks later), 18, 22 (3 weeks later), 25, and 29 (4 weeks later) after completion of the treatment. A relative tumor volume (RTV) to the tumor volume at the start of the test was obtained for each mouse. FIG. 1 shows the mean RTV and the standard deviation (S.D.) in each group as a tumor growth curve. The mean tumor growth inhibition rate (IR; %) in each treatment group based on the control group was obtained by using the following numerical formula 2 on days 15, at the end of the treatment period, and 29 at 4 weeks later and shown in Table 1.

Tumor volume(mm$^3$)=(major axis)× (minor axis)$^2$×½     (Numerical formula 1)

Tumor growth inhibition rate (IR, %)=(1−(mean tumor volume of treatment group)/(mean tumor volume of control group))×100     (Numerical formula 2)

TABLE 1

| Group number | Amount of CDHP (mg/kg) | Dose of X-ray irradiation (Gy) | IR(%) Day 15 | IR(%) Day 29 |
|---|---|---|---|---|
| 1 | 0 | 0 | — | — |
| 2 | 2.5 | 0 | 17.2 | −7.9 |
| 3 | 25 | 0 | 9.7 | −15.3 |
| 4 | 0 | 2 | 35.0 | 9.6 |
| 5 | 2.5 | 2 | 41.0 | 24.7* |
| 6 | 25 | 2 | 57.2 | 46.3** |
| 7 | 0 | 5 | 48.7 | 53.5 |

*$p < 0.05$ compared with either of CDHP (2.5 mg/kg) and 2 Gy (Dannet test)
**$p < 0.001$ compared with either of CDHP (25 mg/kg) and 2 Gy (Dannet test)

(d) Test results: 2-Gy X-ray irradiation on the LC-11 tumor strain showed antitumor effects of 41% on day 15 and 25% on day 29. CDHP at both the doses of 2.5 and 25 mg/kg hardly showed any antitumor effect, but significantly enhanced the effect of X-ray by using 2-Gy X-ray irradiation in combination, with antitumor effects of 41% and 57%, respectively, on day 15 and 25% and 46%, respectively, on day 29. This effect was comparable to the antitumor effect of 5-Gy X-ray irradiation alone. That is, it was found that low-dose X-ray irradiation achieved an effect of high-dose X-ray irradiation by using CDHP in combination. Furthermore, no serious adverse drug reactions such as body weight loss and skin disorders were observed in mice receiving the CDHP and X-ray in combination.

Test Example 2

(a) Preparation of test solution: 3-Cyano-2,6-dihydroxypyridine (CNDP) was suspended in a 0.5% (W/V) hydroxypropylmethylcellulose (HPMC) solution at concentrations of 2.5 and 5.0 mg/mL, and the suspension was stirred with a stirrer at room temperature for about 10 minutes and ultrasonicated for about 5 minutes with ice cooling to obtain a drug solution of 25 or 50 mg/kg/day as CNDP.

(b) Method for radiation (X-ray) irradiation: Local irradiation was performed on a human tumor strain transplanted into the right femoral region of the mouse using MBR-1505R Type 2 X-ray Irradiation System of Hitachi Medical Corporation under an irradiation condition (irradiation position) so that exposure per mouse should be 2 Gy or 5 Gy. To prevent systemic irradiation, mice were placed in a storage box made of lead so that only their right leg should be exposed to radiation.

(c) Test: The human lung cancer strain (LC-11) subcutaneously transplanted into the back of a BALB/cA-nu mouse and grown beforehand were removed, cut into small fragments of about $2 \times 2$ mm$^2$ with scissors in physiological saline, and subcutaneously transplanted into the right femoral region of 5 to 6-week-old mice of the same strain with a transplantation needle. The mice were bred for at least 1 to 2 weeks and divided into the control group, the radiation alone group, the drug alone group, and the drug plus radiation group, so that the tumor volume and standard deviation (S.D.) in each group (n=6 per group) should be as uniform as possible. Then, drug administration and X-ray irradiation were initiated. The drug treatment group was orally administered with 0.1 mL of the above-described 5 mg/mL CNDP drug solution per body weight 10 g once daily for 14 consecutive days using a sonde for oral administration. The radiation group was irradiated with 2 Gy or 5 Gy of X-ray within about 1 hour after administration of the CNDP drug solution in the above-described manner on day 1, at the start of the test, and on day 8. Tumor-bearing mice in the control group (non-radiation/non-drug treatment group) and the radiation alone group were orally administered with 0.50 HPMC solution alone in the same manner for 14 consecutive days.

By using the above-mentioned numerical formula 1, the tumor volume of each mouse in each group was obtained prior to the start of treatment experiment, on days 3, 5, 8, (1 week later) and 11 during the treatment period, and day 15 (2 weeks later) after completion of treatment. A relative tumor volume (RTV) to the tumor volume at the start of the test was obtained for each mouse (FIG. 1). Then, the mean tumor growth inhibition rate (IR: %) in each treatment group based on the control group was obtained from these values by using the above-mentioned numerical formula 2 on days 11, during the treatment period, and 15, at the end of the treatment period. The results are shown in Table 2.

TABLE 2

| Group number | Amount of CNDP (mg/kg) | Dose of X-ray irradiation (Gy) | Tumor growth inhibition rate (IR) (%) Day 11 | Day 15 |
|---|---|---|---|---|
| 1 | 0 | 0 | — | — |
| 2 | 50 | 0 | 1.8 | 8.2 |
| 3 | 0 | 2 | 27.2 | 40.1 |
| 4 | 25 | 2 | 44.7 | 54.6 |
| 5 | 50 | 2 | 44.4 | 60.4 |
| 6 | 0 | 5 | 46.1 | 56.2 |

(d) Test results: 2-Gy X-ray irradiation on the LC-11 tumor strain showed antitumor effects of 27% on day 11 and 40% on day 15. CNDP hardly showed any antitumor effect at a high dose of 50 mg/kg, but significantly increased the antitumor effect of 2-Gy X-ray at both the doses of 25 and 50 mg/kg, with antitumor effects of 44.7% and 44.4%, respectively, on day 11 and 54.6% and 60.4%, respectively, on day 15 by using 2-Gy X-ray irradiation in combination. This effect was comparable to the antitumor effect of 5-Gy X-ray irradiation alone (46% on day 11 and 56% on day 15). That is, it was found that low-dose X-ray irradiation achieved an effect of high-dose X-ray irradiation alone by using CNDP in combination. Furthermore, no serious adverse drug reactions such as body weight loss and skin disorders were observed in the mice receiving the CNDP and X-ray in combination.

Comparative Example 1

Radiotherapy Enhancing Effect of Cisplatin

Combination therapy using radiation and cisplatin is one of therapies commonly used in the clinical setting for the treatment of lung cancer. The effect of cisplatin in the combination therapy was verified.
(a) Preparation of test solution I: The cisplatin solution (0.5 mg/mL) available from Bristol-Myers Squibb Company was used as it was. 0.1 mL per mouse body weight 10 g was administered for the dose of cisplatin 5 mg/kg, and 0.125 mL per mouse body weight 10 g was administered for the dose of 7.5 mg/kg.
(b) Method for radiation (X-ray) irradiation: Local irradiation was performed on a human tumor strain transplanted into the right femoral region of the mouse using MBR-1505R Type 2 X-ray Irradiation System of Hitachi Medical Corporation under an irradiation condition (irradiation position) so that exposure per mouse should be 2 Gy or 5 Gy. To prevent systemic irradiation, mice were placed in a storage box made of lead so that only their right leg should be exposed to radiation.
(c) Test: The human lung cancer LC-11 strain subcutaneously transplanted into the back of a BALB/cA-nu mouse and grown beforehand were removed, cut into small fragments of about 2×2 mm$^2$ with scissors in physiological saline, and subcutaneously transplanted into the right femoral region of 5 to 6-week-old mice of the same strain with a transplantation needle. The mice were bred for at least 1 to 2 weeks and divided into the control group, the radiation alone group, the drug alone group, and the drug plus radiation group, so that the tumor volume and standard deviation (S.D.) in each group (n=6 per group) should be as uniform as possible. Then, drug administration and X-ray irradiation were initiated. For the drug treatment group, 0.1 mL per body weight 10 g of a cisplatin solution for the dose of 5 mg/kg or 0.125 mL per body weight 10 g of this solution for the dose of 7.5 mg/kg was administered into the caudal vein on day 1. The radiation group was irradiated with 2 Gy of X-ray in the above-described manner on day 1, at the start of the test, and on day 8. For tumor-bearing mice in the control group (non-radiation/non-drug treatment group) and the radiation alone group, physiological saline was administered into the caudal vein on day 1.

By using the above-mentioned numerical formula 1, the tumor volume of each mouse in each group was obtained prior to the start of treatment experiment, on days 3, 5, 8 (1 week later) and 11 during the treatment period, and days 15 (2 weeks later), 18, 22 (3 weeks later), 25, and 29 (4 weeks later) after completion of treatment. A relative tumor volume (RTV) to the tumor volume at the start of the test was obtained for each mouse. Then, the mean tumor growth inhibition rate (IR; %) in each treatment group based on the control group was obtained by using the above-mentioned numerical formula 2 on days 15, at the end of the treatment period, and 29, at 4 weeks later, and shown in Table 3.

TABLE 3

X-ray irradiation sensitizing effect of cisplatin

| Group number | Dose of X-ray irradiation (Gy) | Amount of CDDP (mg/kg) | IR (%) Day 15 | Day 29 |
|---|---|---|---|---|
| 1 | — | — | — | — |
| 2 | 2 | — | 37.5 | 32.3 |
| 3 | — | 5.0 | 39.9 | 45.6 |
| 4 | 2 | 5.0 | 53.8 | 46.8 |
| 5 | — | 7.5 | 55.8 | 60.2 |
| 6 | 2 | 7.5 | 54.6 | 66.8 |
| 7 | 5 | — | 45.1 | 59.9 |

(d) Test results: Combination use of CDDP 5 mg/kg or 7.5 mg/kg and 2-Gy X-ray irradiation did not significantly enhance antitumor effects compared with treatment with CDDP alone, and the radiotherapy enhancing effect of CDDP appeared to be very weak in a series of examinations using the human lung cancer LC-11 strain.

Test Example 3

Effect of Irradiation on Disorders of Normal Tissues (Normal Skin)

(a) Preparation of test solution: CDHP was suspended in a 0.5% (W/V) HPMC solution at a concentration of 5.0 mg/mL, and the suspension was stirred with a stirrer at room temperature for about 10 minutes and ultrasonicated with ice cooling for about 5 minutes to obtain a drug solution of 50 mg/kg/day as CDHP.

(b) Method for X-ray irradiation: Local irradiation was performed on the right femoral region of the mouse using MBR-1505R Type 2 X-ray Irradiation System of Hitachi Medical Corporation under an irradiation condition (irradiation position) so that exposure per mouse should be 20 Gy. To prevent systemic irradiation, mice were placed in a storage box made of lead so that only their right leg should be exposed to radiation.

(c) Test: Six to 8-week-old BALB/cA-nu mice were divided into the control group, the radiation alone group, and the drug plus radiation group, each consisting of 6 animals, and drug administration and X-ray irradiation were initiated. Since the drug (CDHP) itself does not induce any antitumor effect or adverse drug reaction even when orally administered everyday, the drug alone group was omitted. The radiation group was irradiated with 20 Gy of X-ray/mouse on day 1, at the start of the test, and on day 3. The drug plus radiation group was irradiated with X-ray on days 1 and 3 as described above and orally administered with 0.1 mL of the CDHP drug solution per body weight 10 g once daily for 7 consecutive days using a sonde for oral administration. This group was irradiated with 20 Gy of X-ray within about 1 hour after administration of CDHP drug solution in the above-described manner on days 1 and 3. Normal mice in the control group (non-radiation/non-drug treatment group) were orally administered with 0.5% HPMC solution alone in the same manner for 7 consecutive days.

(d) Determination of severity of skin disorders: From 7 days after the end of the test, severity of skin disorders in the femoral region caused by irradiation was determined by the method of Douglas, et al. (Douglas B G, et al.: The effect of multiple small doses of X-rays on skin reactions in the mice and a basic interpretation. Radiation Res., 66: 401-426, 1976.).

Figure 2:
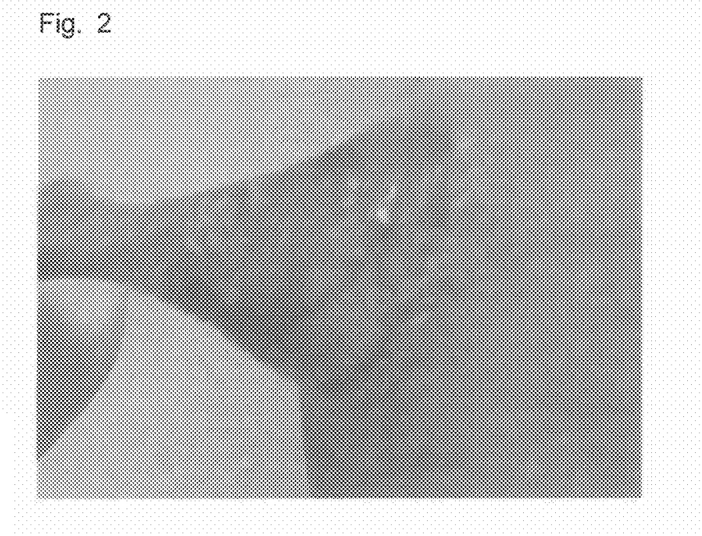
FIG. 2 is a photo showing skin conditions of the femoral region in the radiation alone group in Test Example 3 (on day 14)
Figure 3:
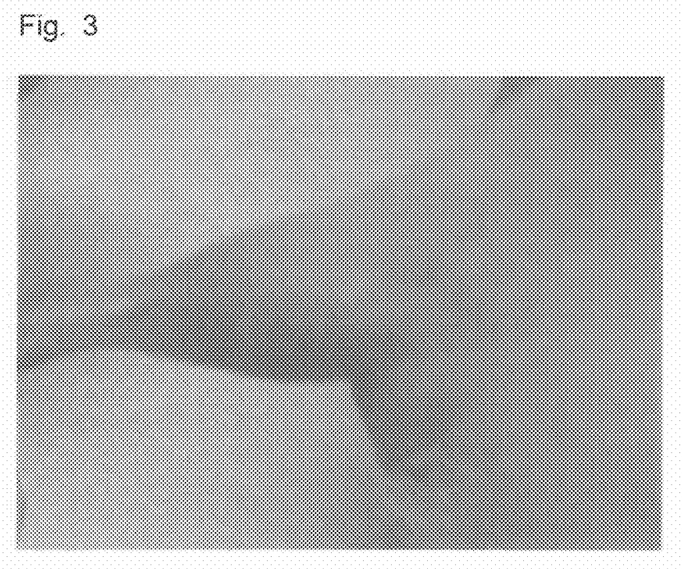
FIG. 3 is a photo showing skin conditions of the femoral region in the CDHP plus radiation group in Test Example 3 (on day 14)
Figure 4:
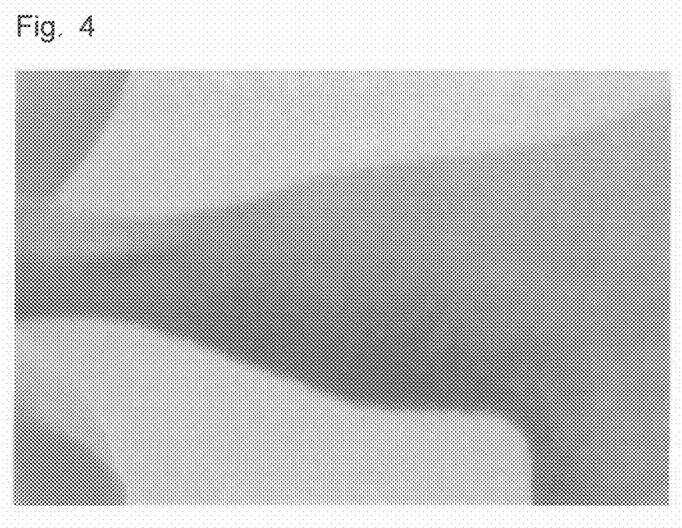
FIG. 4 is a photo showing skin conditions of the femoral region in the control group in Test Example 3 (on day 14).

(e) Test results: In the radiation alone group, dehydration and keratinization of the skin (grades 1.0 to 1.5) and skin surface loss (grades 2.5 to 3.0) started to develop on day 10, and skin disorders of grades 1.5 or higher were observed in all the 6 animals after day 14 (see FIG. 2). On the other hand, mild disorders (redness, swelling) were observed only in 1 or 2 mice in the CDHP plus radiation group, and no abnormality was noted in the other mice (see FIG. 3). No skin disorder was observed in the control group (see FIG. 4).

The above results revealed that CDHP had actions of enhancing the antitumor effect of X-ray irradiation on tumor and not exacerbating but preventing or reducing disorders caused by radiation in normal tissues (here normal skin).

Preparation Example 1

Tablets

| | |
|---|---|
| CDHP | 18 mg |
| Starch | 110 mg |
| Magnesium stearate | 17 mg |
| Lactose | 40 mg |
| Total | 185 mg |

Tablets of 185 mg/tablet were prepared with the above mixture composition according to a usual method.

Preparation Example 2

Tablets

| | |
|---|---|
| CNDP | 12 mg |
| Lactose | 54 mg |
| Crystalline cellulose | 20 mg |
| Magnesium stearate | 5 mg |
| Talc | 3 mg |
| Methylcellulose | 10 mg |
| Total | 104 mg |

Tablets of 104 mg/tablet were prepared with the above mixture composition according to a usual method.

Preparation Example 3

Granules

| | |
|---|---|
| CDHP | 58 mg |
| Lactose | 340 mg |
| Corn starch | 450 mg |
| Hydroxypropylmethylcellulose | 10 mg |
| Total | 858 mg |

Granules were prepared with the above mixture composition according to a usual method.

Preparation Example 4

Suppository

| | |
|---|---|
| CDHP | 110 mg |
| Witepsol W-35 | 900 mg |
| Total | 1010 mg |

A suppository was prepared with the above mixture composition according to a usual method.

The invention claimed is:

1. A method of enhancing radiotherapy effects for tumor treatment, consisting of:
administering to a subject in need thereof an amount, effective for enhancing radiotherapy effects, of a pyridine compound represented by the formula (1):

(1)

wherein
$R^1$, $R^2$, and $R^4$ may be the same or different from one another and represent a hydrogen atom, hydroxy group, or protected hydroxy group, with the proviso that $R^1$, $R^2$, and $R^4$ are not all a hydrogen atom, and
$R^3$ represents a halogen atom, amino group, carboxyl group, carbamoyl group, cyano group, nitro group, alkyl group having 1 to 6 carbon atoms, alkenyl group having 2 to 6 carbon atoms, or carbonyl group containing an alkoxy group having 1 to 6 carbon atoms;
and irradiating said subject, thereby the effects of irradiation are enhanced.

2. The method according to claim 1, wherein
$R^1$ and $R^2$ may be the same or different from each other and represent a hydroxy group or a protected hydroxy group, and
$R^4$ represents a hydrogen atom.

3. The method according to claim 1, wherein
$R^1$ and $R^4$ may be the same or different from each other and represent a hydroxy group or a protected hydroxy group, and
$R^2$ represents a hydrogen atom.

4. The method according to claim 1, wherein
two of $R^1$, $R^2$, and $R^4$ represent a hydroxy group and the remaining group represents a hydrogen atom, and
$R^3$ represents a halogen atom or a cyano group.

5. The method according to claim 1, wherein
$R^1$ and $R^2$ represent a hydroxy group,
$R^3$ represents a chlorine atom, and
$R^4$ represents a hydrogen atom.

6. The method according to claim 1, wherein
$R^1$ and $R^4$ represent a hydroxy group,
$R^3$ represents a cyano group, and
$R^2$ represents a hydrogen atom.

7. The method according to claim 1, wherein said subject has a malignant tumor.

8. The method according to claim 7, wherein said malignant tumor comprises at least one tumor selected from the group consisting of head and neck cancer, esophageal cancer, gastric cancer, colorectal cancer, liver cancer, gallbladder cancer, bile duct cancer, pancreatic cancer, lung cancer, breast cancer, bladder cancer, prostate cancer, cervical cancer, brain tumor, malignant lymphoma, acute leukemia, chronic leukemia, medulloblastoma, retina retinoblastoma, neuroblastoma, Wilms' tumor, Hodgkin's disease, multiple myeloma, plasmacytoma, thymoma, basal cell cancer, squamous cancer, Ewing's tumor, thyroid cancer, ovary cancer, salivary gland cancer, teratoma, malignant melanoma, neuroglioma, renal cell carcinoma, and osteosarcoma.

9. The method according to claim 7, wherein said malignant tumor comprises at least one tumor selected from the group consisting of head and neck cancer, esophageal cancer, gastric cancer, colorectal cancer, liver cancer, lung cancer, pancreatic cancer, and breast cancer.

10. The method according to claim 7, wherein said malignant tumor comprises at least one tumor selected from the group consisting of lung cancer and pancreatic cancer.

11. The method according to claim 1, wherein said subject is irradiated with a X-ray.

12. The method according to claim 1, wherein the pyridine compound is administered in the amount of 0.05-100 mg per kg of body weight.

13. The method according to claim 1, wherein the pyridine compound is administered in the amount of 0.1-50 mg per kg of body weight.

* * * * *